United States Patent [19]

Shaw

[11] Patent Number: 5,389,076

[45] Date of Patent: Feb. 14, 1995

[54] SINGLE USE MEDICAL DEVICE WITH RETRACTION MECHANISM

[76] Inventor: Thomas J. Shaw, 1510 Hillcrest, Little Elm, Tex. 75068

[21] Appl. No.: 222,888

[22] Filed: Apr. 5, 1994

[51] Int. Cl.$^6$ .............................................. A61M 5/32
[52] U.S. Cl. ................................... 604/110; 604/195; 604/218
[58] Field of Search ............... 604/110, 187, 192, 195, 604/198, 218, 263

[56] References Cited

U.S. PATENT DOCUMENTS

| | | | |
|---|---|---|---|
| 3,306,290 | 2/1967 | Weltman. | |
| 4,747,831 | 5/1988 | Kulli | 604/110 |
| 4,838,863 | 6/1989 | Allard et al. | 604/110 |
| 4,838,869 | 6/1989 | Allard | 604/195 |
| 4,841,985 | 6/1989 | Wanamaker | 128/763 |
| 4,874,382 | 10/1989 | Lindemann et al. | 604/195 |
| 4,904,242 | 2/1990 | Kulli | 604/110 |
| 4,955,870 | 9/1990 | Ridderheim et al. | 604/195 |
| 4,994,034 | 2/1991 | Botich et al. | 604/110 |
| 5,019,044 | 5/1991 | Tsao | 604/110 |
| 5,046,508 | 9/1991 | Weissler | 128/763 |
| 5,049,133 | 9/1991 | Pascual | 604/110 |
| 5,053,010 | 10/1991 | McGary et al. | 604/110 |
| 5,064,419 | 11/1991 | Gaarde | 604/195 |
| 5,084,029 | 1/1992 | Tagliaferri et al. | 604/195 |
| 5,092,853 | 3/1992 | Couvertier, II | 604/195 |
| 5,104,378 | 4/1992 | Haber et al. | 604/110 |
| 5,114,410 | 5/1992 | Batlle | 604/195 |
| 5,120,310 | 6/1992 | Shaw | 604/110 |
| 5,180,370 | 1/1993 | Gillespie | 604/110 |
| 5,188,599 | 2/1993 | Botich et al. | 604/110 |
| 5,201,710 | 4/1993 | Caselli | 604/110 |
| 5,211,628 | 5/1993 | Marshall | 604/110 |
| 5,324,265 | 6/1994 | Murray et al. | 604/110 |
| 5,330,430 | 7/1994 | Sullivan | 604/195 X |
| 5,330,440 | 7/1994 | Stanners et al. | 604/195 |

FOREIGN PATENT DOCUMENTS 146773 12/1990 Japan.

OTHER PUBLICATIONS

Disappearing needle, Mar. 22, 1993 Design News, p. 58.

Primary Examiner—John D. Yasko
Attorney, Agent, or Firm—Harris, Tucker & Hardin

[57] ABSTRACT

A single use retractable syringe has three main parts which are coaxially arranged. An outer barrel is fitted with a slidable plunger and an elongated needle rod is carried within the plunger and biased for retraction. In the unretracted position of the needle rod, an injection needle is extended from the front of the barrel. The needle rod is held in the unretracted position by a resilient ring member frictionally mounted on one larger part of the needle rod just behind a reduced size front part of the needle rod. The needle communicates with a variable fluid chamber behind the resilient ring member below the front end of the plunger. After an injection, further depression of the plunger pushes the resilient ring member forward and off the larger diameter portion of the needle rod to release the needle rod which is biased to retract along with the needle into the plunger. The needle rod may be biased in the retraction direction by a spring or by a vacuum in the plunger behind the needle rod. The device is simple in operation and especially suited for mass production and robotic assembly. Retraction is reliable and permanent.

29 Claims, 4 Drawing Sheets

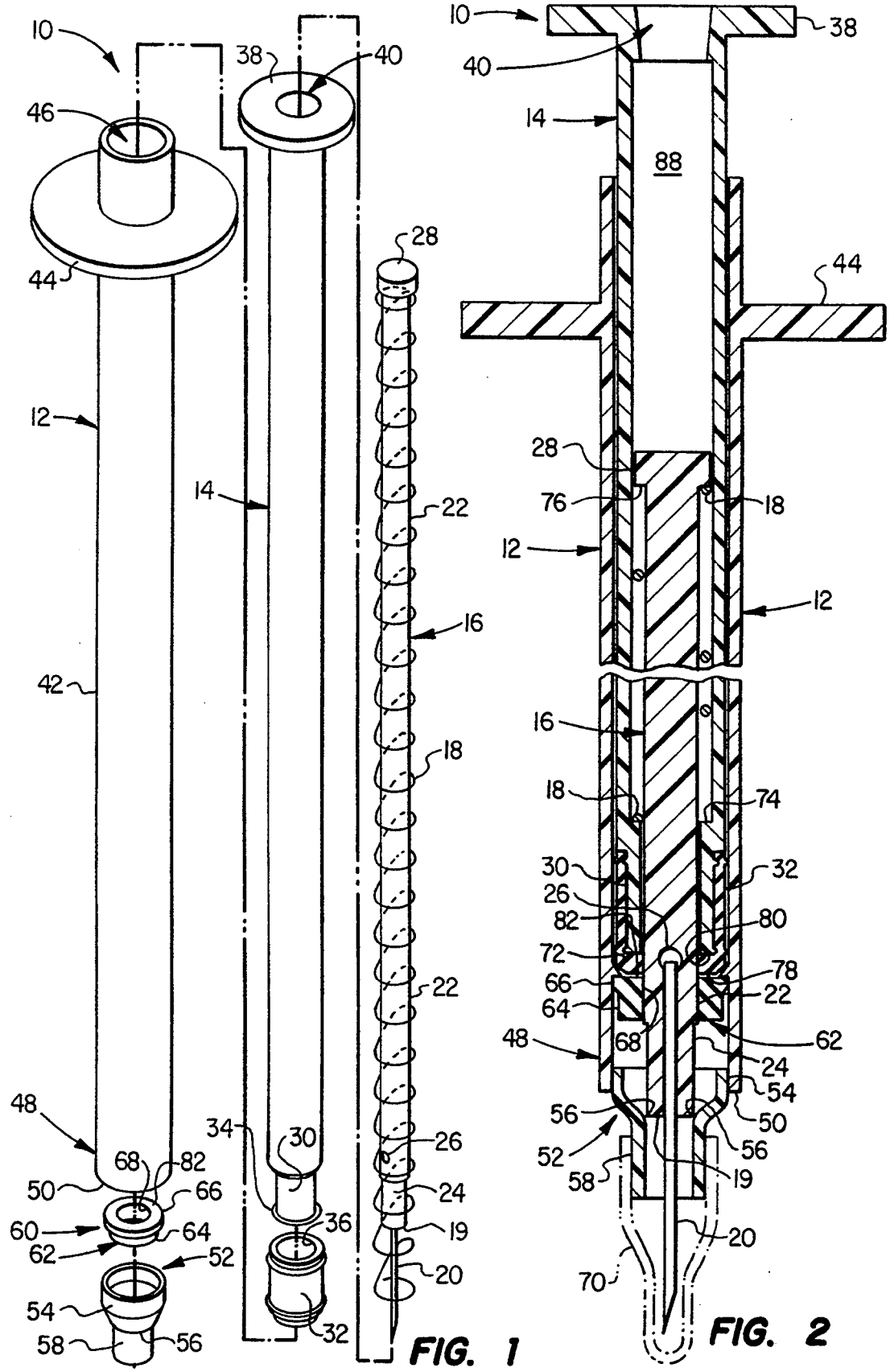

1

SINGLE USE MEDICAL DEVICE WITH RETRACTION MECHANISM

FIELD OF THE INVENTION

This invention relates to a medical device, and more particularly, to a single use retractable syringe having an automatically retracting needle which is permanently retracted after one use.

BACKGROUND OF THE ART

A major cause for the spread of AIDS in the general population is the presence of IV drug users who share and reuse hypodermic syringes to inject drugs. Infection can also be spread from AIDS patients in hospitals and medical facilities through accidental needle sticks with needles used on infected patients. Used syringes with extended needles present a risk not only to medical personnel but also to sanitation employees and others in the disposal chain.

There are a number of syringes of different designs which have needles which will retract at the end of the injection cycle. Most of these have never reached the market because of various deficiencies. Prime among the usual deficiencies of the prior art are problems of complexity, reliability and cost. Medical syringes are produced and used by the millions every day. Cost is a significant factor both in manufacture of the parts and assembly of the device.

A principal problem with the prior art devices is the fact that in order to retract the needle, some part or parts must flex and bend, break or a diaphragm must be ruptured at a particular stage in the operation. A number of these prior art references are briefly discussed in my co-pending patent application Ser. No. 08/125,292, filed Sep. 21, 1993, which is incorporated by reference. The problems of complexity, reliability and cost are intertwined since things that are more complex generally have a higher failure rate and cost than do simpler devices. This is particularly true in the miniature one cc syringes which are the most commonly manufactured and used syringes. It is far more difficult to miniaturize complex retraction mechanisms and still have the parts function effectively and reliably.

It would be highly desirable to produce a medical device, in the form of a syringe, which meets the requirements mentioned. Suitable syringes should at least 1) maintain the same capacity to hold fluids and offer accurate incremental measurement of fluid as compared with standard syringes; 2) permit one-handed use so that the other hand of the health care worker is free to assist in holding the patient; 3) retract fully after use and thereby eliminate needle sticks because of mistaken belief that retraction has occurred when, in fact, it hasn't; 4) indicate prior use; 5) be extremely reliable, even over a wide range of temperature; 6) be easily assembled for mass production; 7) be manufactured at extremely low cost; and 8) operate reliably under a variety of circumstances. The invention disclosed herein meets these requirements and more.

SUMMARY OF THE INVENTION

A single use medical device has a retraction mechanism equipped with a needle for collecting and injecting fluid. The medical device is in the form of a syringe having an elongate hollow outer body, a plunger selectively movable in sliding contact with the interior surface of the outer body and a needle holding member comprising an elongated needle rod having a needle extending from a front end thereof. The needle rod is slidingly mounted within the hollow interior of the plunger, along with a biasing element which biases the needle rod and needle to a retracted position entirely within the outer body.

A resilient release element comprising a ring member is formed from a rubber or elastomeric material and frictionally mounted near the front end of the needle rod. The release element cooperates with the outer body to hold the needle rod with the needle extended in the unretracted position while the plunger is movable relative to the outer body. The needle rod remains stationary while the plunger is moved to collect or inject fluid. The retainer member holds the needle rod with a friction force that exceeds the retraction force on the needle rod provided by the biasing element which may comprise a coil compression spring.

The principle of operation is different from other syringes. There are no intricate parts and none of the parts need to flex, bend, break or tear. The only thing preventing the needle from retracting in response to the biasing element is the frictional engagement between the retainer member and the needle rod at the front of the syringe. After the syringe is filled by withdrawing the plunger to create a variable chamber in the syringe body behind the retainer member, the fluid is injected by depressing the plunger. A piston on the front portion of the plunger moves forward to collapse the varying chamber and expel the fluid through the needle. The variable chamber is in fluid communication with an opening in the needle through an opening in the needle rod which is located above the retainer member. After substantially all the fluid is expelled, further depression of the plunger moves the retainer member forward until the retainer member is dislodged from a portion of the needle rod with which it has been in frictional engagement to a place where the frictional engagement becomes very substantially less or none and the needle rod is released from the retainer member.

In the preferred embodiment, the needle rod has a front portion and a back portion wherein the front portion is smaller than the back portion. Part of the back portion of the needle rod is positioned within the plunger at all positions of the plunger while moving the plunger during use of the device for collecting and injecting fluid. Retraction is initiated by relative movement of the retainer member in the forward position from the back portion to the smaller front portion of the needle rod caused by force applied by the front of the plunger to the retainer member at the end of the plunger's stroke. Retraction occurs when the release element loses its frictional holding force in excess of the retraction force produced by the biasing element as a result of the retainer member being pushed to the smaller front portion of the needle rod whereupon the needle rod is released and retracted.

The varying chamber for injection fluid is created behind the retainer member by rearward movement of the plunger away from the retainer member. The varying chamber for injection fluid is sealed by the retainer member and by a front head portion of the plunger having a resilient piston which slides with the plunger inside the outer body. Thus, it may be said that during use of the device with the needle in the extended unretracted position, the back portion of the needle rod passes through the front head portion of the plunger and is sealed thereby. Although the drawings show the needle rod is sealed by a cup-shaped front face of the piston having an opening therethrough, it is also within the contemplation of the invention to slidingly seal the front end portion of the plunger and the needle rod by conventional means, such as an "O" ring or similar seal on the inside of the front head portion of the plunger in contact with the cylindrical outer surface of the needle rod. In fact, this seal offers the only frictional resistance to retraction of the needle rod once the resilient retaining ring is dislodged from the larger diameter portion of the needle rod below the piston.

The back portion of the needle rod terminates in a glide head which loosely slides within the plunger and has a shoulder for one end of a coil spring which applies retraction force in a retraction direction to the needle rod. The other end of the compression spring is supported by a support surface formed on the inside of the plunger just behind the piston. The back end of the plunger has a thumb flange which is either closed or has a restriction to prevent backward removal of the needle rod after retraction has occurred. In the preferred embodiment, the flange at the back of the plunger has a coaxial tapered opening to facilitate assembly in a unique manner by introducing the needle end of the needle rod, surrounded by the compression spring, through the opening in the forward direction. The sliding glide head is slightly larger than the restricted opening at the back of the plunger so that it can be forced forwardly through the opening in a forced fit and cannot thereafter be removed.

In an alternative embodiment, the sliding glide head on the back end of the needle rod may be made of a resilient material which slidingly seals the inner surface of the plunger. The back of the plunger is then equipped with a plug member which can be punctured by a sharp needle connected to a vacuum source. The plug member is of a material which seals itself as the needle is withdrawn. This permits drawing of a vacuum in a chamber behind the modified guide head sufficient to apply the required retraction force to the needle rod. In this embodiment, the spring is omitted and it is not necessary to form the support surface on the front of the plunger that would otherwise hold the spring. In other words, the plunger can be essentially cylindrical and the assembly of the needle rod is through the opening in the front of the plunger by passing the modified glide head through the opening.

It is necessary to provide a stop means at the tip of the syringe body located in the path of the needle rod to arrest forward movement of the needle rod. This is necessary to prevent the needle rod from moving forward from the unretracted position when the plunger is pressed to dislodge the retainer member from the larger portion at the front of the needle rod. The stop surface can be provided through a separate tip member fixed to the end of the elongated syringe barrel and together with another stop surface located behind the retainer member, serves to prevent the needle rod from moving in the axial direction while the plunger is being moved to transfer fluid to or from the variable chamber behind the retainer member. A variation of the tip member may include a shoulder that permits it to be set against the end of the hollow outer body of the syringe which helps to precisely locate the required stop surface. In a further variation, a disk-like member having a laterally extending slot may be placed over the needle and force fit into the tip end of the syringe barrel and fixed in place. The upper surface of the disk serves as a stop member to prevent forward movement of the needle rod with the needle extended from the tip of the syringe in the unretracted position.

The medical device of the invention offers major advantages arising from the inventive concept. It permits a great reduction in complexity by employing fewer parts which themselves are well-suited to molding as single pieces which are easily assembled. Assembly can be completed by axial movements from the front or back without regard to angular orientation and without the necessity of lateral movements. This makes the single use syringe ideally suited for robotic automated assembly in high volume. The parts do not require things that break, flex, tear or need to be hooked together, and there are no critical tolerances.

BRIEF DESCRIPTION OF THE DRAWINGS

FIG. 1 is an exploded perspective view of the preferred embodiment illustrating its simplicity;

FIG. 2 is a cross-sectional view of the assembled medical device of FIG. 1 in the shipping position with a protective cap over the extended needle; and the plunger in the depressed starting position;

DETAILED DESCRIPTION OF THE INVENTION

Figure 3:
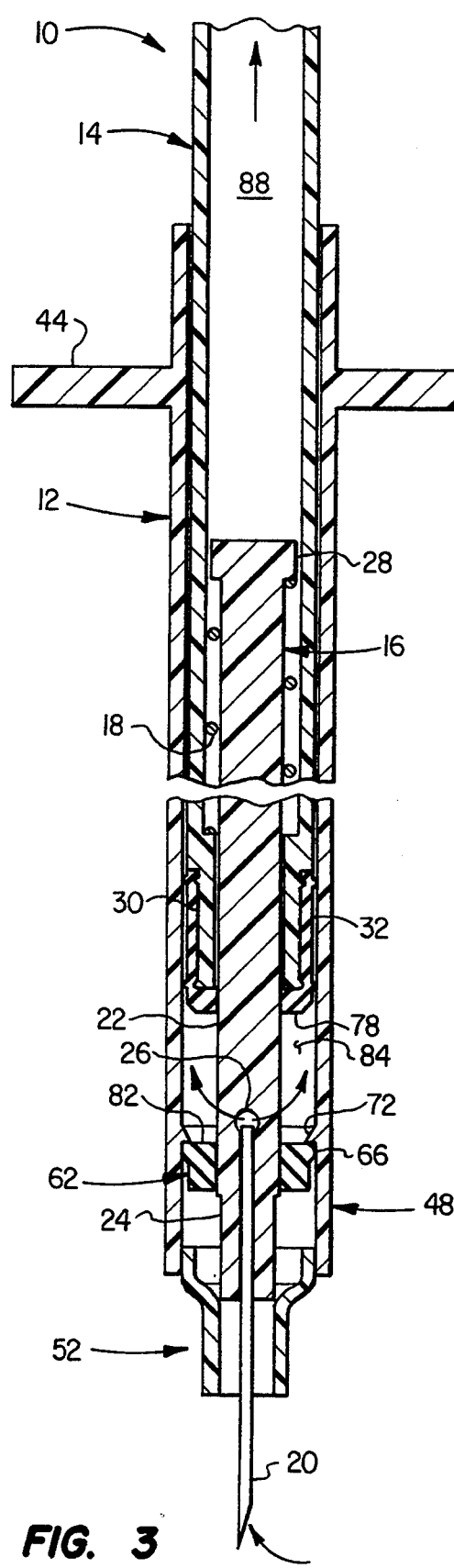
FIG. 3 is a cross-sectional view of the embodiment of FIG. 2 with the plunger moving backward and drawing fluid through the needle into the variable chamber below the head of the plunger.

The single use medical device is referred to generally by the reference numeral 10. A perspective view of the device 10 is shown in FIG. 1. The device 10 as assembled ready for shipping is shown in cross-section in FIG. 2. Syringe 10 has an outer body 12 which is an elongate hollow body, preferably in the form of a cylinder. Outer body 12 contains a retraction mechanism and a plunger 14 slidably axially in the outer body. The retraction mechanism includes a needle holding member comprising an elongated needle rod 16. Needle rod 16 is surrounded by a biasing element comprising spring 18. The front end 19 of needle rod 16 has an embedded hollow injection needle 20. Needle rod 16 has a back portion 22 and a front portion 24 which is of a lesser diameter than the back portion 22. In the circular form of the needle rod, this corresponds to back portion 22 being of one diameter and the front portion 24 being of a stepped-down, lesser diameter. The front of the back portion 22, just behind front portion 24, has a opening 26 for fluid spaced behind a demarcation which separates the front portion 24 and the back portion 22. The demarcation is a step down to the lesser diameter front portion 24. Opening 26 is an opening for fluid in fluid communication with needle 20. In the preferred form of the needle rod, the back portion 22 is cylindrical and extends rearwardly away from the needle, terminating in a sliding guide head 28 at the back end of the needle rod. Guide head 28 is larger than back portion 22 and serves as an abutment stop for the back end of spring 18. Guide head 28 slides loosely along the inside surface of plunger 14 to guide and maintain the lateral position of the needle rod.

Elongated needle rod 16 is coaxially installed in the hollow interior of plunger 14. Plunger 14 is preferably a hollow cylindrical plunger having a front head portion 30 having a resilient piston 32. The piston has an opening 36 to fit removably over flange 34. Piston 32 is designed to be removably force fit over front end flange 34 at the front of the plunger. Front end portion 30 is hollow to axially accommodate the needle rod and needle, which when installed also passes through piston 32 in a manner indicated in FIG. 2. The rear end of plunger 14 is equipped with a ranged end 38 having an axially centered opening 40. The opening 40 is designed to forcibly accept the coaxially installed needle rod 16 in a manner to be subsequently described.

Outer body 12 has an outer surface 42 having a rear portion equipped with flange 44. An opening 46 at the rear extends through the inside of outer body 12. Outer body 12 may be referred to as the barrel of the syringe. It has a front end portion 48 which terminates at a front end 50. The front of outer body 12 is equipped with the tip member 52 having an attachment surface 54 tapering to a shoulder 56 and a tip extension 58 below shoulder 56.

A release element generally designated by the reference numeral 60 is a separate retainer member 62 slidingly mounted on the back portion 22 of the needle rod just behind lesser diameter portion 24. In the assembly, release element 60 is mounted interiorly of the front end portion 48 of outer body 12. Retainer member 62 has a body 64, a peripheral land 66 and an axial opening 68 which frictionally engages the back portion 22 of needle rod 16. When installed, land 66 may preferably form a sliding seal against the inner wall of outer body 12.

The assembly is best appreciated by reference to FIGS. 2-5. In the assembled condition of FIG. 2, tip member 52 is affixed to front or tip end portion 48, at the front thereof, via attachment surface 54. Shoulder 56 serves as a stop in the path of the end 19 of the needle rod to prevent forward movement thereof. Needle 20 is extended in the unretracted position through tip extension 58 and covered with a removable protective cap 70. Needle 20 is in fluid communication directly or through a passage-way with opening 26 in the needle rod. Separate retainer member 62 is frictionally mounted on back portion 22 of needle rod 16. Retainer member 62 is located on the needle rod just behind lesser diameter front portion 24 and below opening 26.

In the preferred embodiment, retainer member 62 is a resilient ring member in which body 64 is smaller in diameter than the inside of outer body 12 and whereas the land 66 sealingly engages the inside of outer body 12. A restriction 72 on the inner surface of outer body 12 is somewhat exaggerated in size in the drawings. Restriction 72 could be a small annular surface or circumferentially spaced tooth-like projections with a sloping surface on one side and a small stop surface or abutment on the other side. Retainer member 62 fits up against restriction 72 on the inside of outer body 12. Restriction 72 prevents the retainer member from moving rearwardly in a retraction direction. Since the retainer member frictionally engages the larger diameter back portion of the needle rod, the needle rod is prevented by the retainer member from moving in the retraction direction.

Piston 32 is removably mounted on end portion 30 by one or more flanges 34 as shown in FIG. 2. Immediately behind the piston, the plunger is formed to include a shelf or shoulder 74 which serves to stop the front end of the spring 18. The back end of spring 18 is stopped by a shoulder 76 under sliding glide head 28. Thus, it can be seen that retainer member 62 frictionally engages the needle rod and in cooperation with the restriction on the inside surface of outer body 12, produces a frictional holding force which exceeds axial retraction force directed against the end of the needle rod by the biasing element, spring 18. In the assembly of FIG. 2, the needle rod and needle are held in the extended unretracted position by retainer ring 62 in opposition to a retraction force applied in the retraction direction by the spring member.

Resilient piston 32 slidingly seals the interior wall of the outer body or barrel of the syringe in the usual manner. Resilient piston 32 is a cup-shaped member having a laterally extending face 78 and an opening 80 through which back portion 22 of the needle rod sealingly passes with the needle rod and needle extended in the unretracted position. Retainer member 62 has a laterally extending face 82. Face 82 of the retainer member and face 78 of the piston come together to expel substantially all of the fluid from the syringe when the plunger is depressed, said fluid being compressed to flow into the opening 26 and thence to the end of needle 20. Upon further depression of the plunger, retainer 62 is forced off back portion 22 of the needle rod and over the smaller diameter reduced section 24 where it no longer frictionally engages the needle rod and the biasing element drives the needle rod and needle into the retracted position within plunger 14.

FIG. 3 illustrates the formation of a variable chamber 84 in outer body 12 between face 82 of the retainer ring 62 and face 78 of piston 32. As the plunger is withdrawn, a partial vacuum is created in variable chamber 84. Fluid may be drawn into variable chamber 84 through needle 20 as indicated by the arrows. As plunger 14 is drawn back, spring 18 is compressed. While the compression of spring 18 increases the retraction force in the retraction direction, it is still less than the friction force applied by retainer ring 62 operating on needle rod 16. The needle rod may be longer than illustrated to make sure there is sufficient fluid capacity in the syringe. The length of the plunger 12 may be adjusted to ensure that the entire needle will be retracted into the plunger when the syringe is "fired" by pushing the retainer member off the larger diameter back portion of the needle rod by depression of the plunger. In all circumstances, part of the back portion of the needle rod is positioned within the plunger at all positions of the plunger during filling and injecting operations.

It can be seen that retainer member 62 and tip member 52 restrain the needle rod 16 and needle 20 in a fixed extended unretracted position within outer body 12. The plunger is free to move axially in simultaneous sliding seal contact with the inner wall of outer body 12 and the outer surface of needle rod 16.

Figure 4:
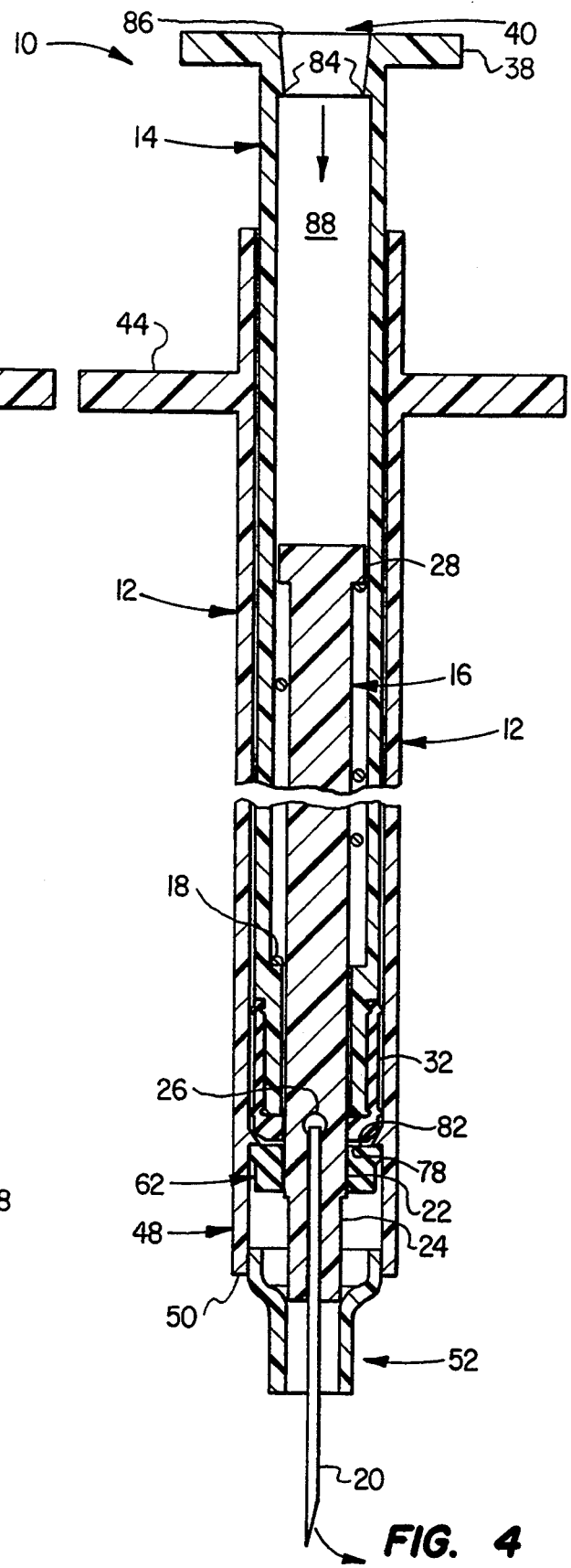
FIG. 4 is a cross-sectional view of the embodiment of FIG. 4 at the end of the injection as the retraction motion is beginning.

After the filling operation illustrated in FIG. 3 in which injection fluid is drawn into variable chamber 84, any air bubbles are removed and the dose is adjusted by expelling excess fluid. The injection is made by depressing plunger 14 which expels the fluid in front of piston 32 through needle 20. The syringe is returned to the position of FIG. 4. In the position of FIG. 4, substantially all the fluid is expelled from variable chamber 84 and surfaces 78 and 82 are brought close together where they collectively define the bottom of the variable chamber 84. The medical device is now ready for automatic retraction which occurs by continued depression of plunger 14. It should be noted that the syringe size is greatly exaggerated in the drawing, being probably 2–3 times the size of an actual three cc syringe, and probably more than 3–4 times the size of an actual one cc syringe. Therefore, the retraction mechanism is very small and release element 62 is very thin. Consequently, only a very small selective movement of the plunger is required after the last fluid is expelled in order to transfer the resilient retainer 62 from the extreme front of the back portion 22 of needle rod 16 to the stepped down front portion 24. Opening 68 in retainer member 62 is larger than the diameter of front portion 24 of the needle rod so that when the retainer member is moved over stepped down portion 24, it no longer frictionally holds the needle rod against the retraction force applied by spring 18 and needle rod 16 is released and retracted into the plunger along with needle 20.

Figure 5:
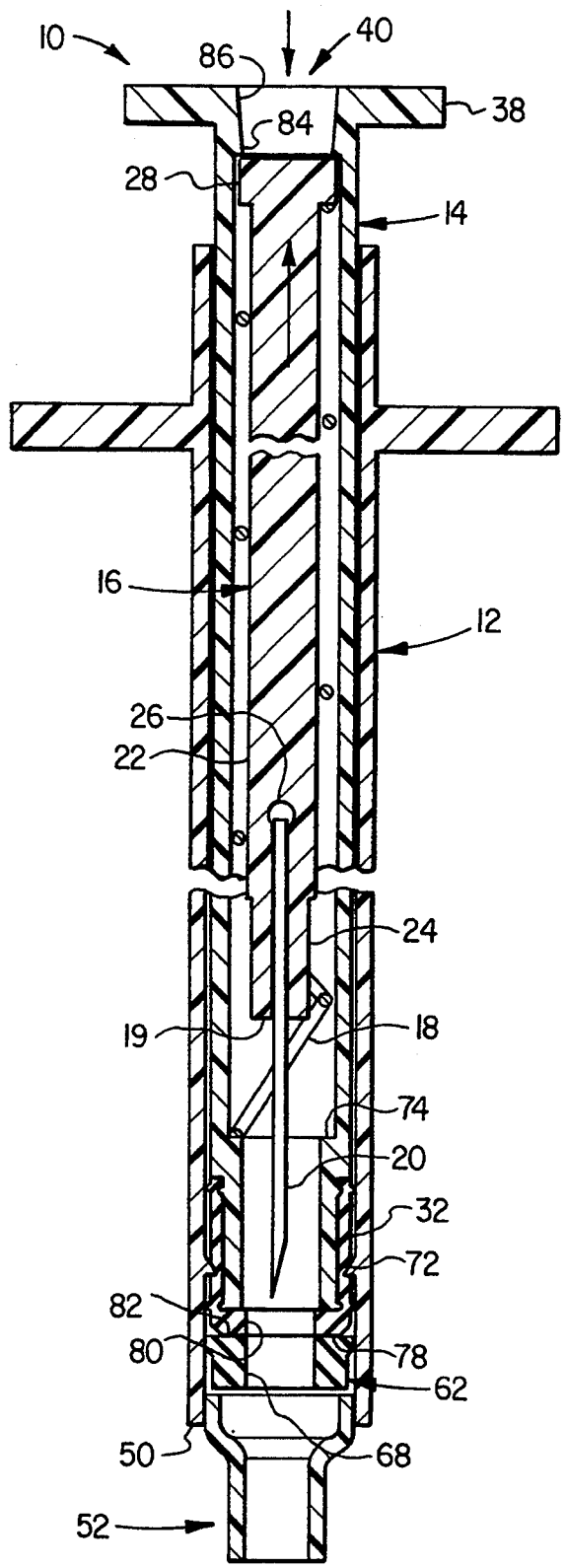
FIG. 5 is a cross-sectional view of the embodiment of FIG. 4 in the retracted condition of the needle resulting from further depression of the plunger a short distance beyond the position of FIG. 4.

FIG. 5 illustrates the retracted position of the syringe immediately after the retainer member 62 is pushed from the position of FIG. 4 by the end of the plunger from the back portion 22 to the front portion 24 of needle rod 16. The plunger is depressed beyond the position of FIG. 4 to slide down over restriction 72 and push retainer member 62 toward the front of the outer body. Retainer 62 is prevented from escaping by interference with tip member 52. Needle rod 16 is released and driven back to the extreme rear of the plunger by spring 18. The back of guide head 28 is captured within the back of the plunger by a constriction 84 at the bottom of opening 40 in the back of the plunger.

The invention is especially suited for easy automated and inexpensive assembly which is a major advantage over other retractable syringes. Ease of assembly and reliability is facilitated by a relatively small number of parts which are well suited for mass production. The separate parts are best visualized by refrence to FIG. 1. Barrel 12, plunger 14 and needle rod 16 are each molded in one piece. Because they have no internal undercuts, slow and expensive collapsible core pin technology is not required.

As seen in FIGS. 4 and 5, the back of plunger 14 has an opening 40 with an entrance 86 larger than guide head 28. Opening 40 tapers inwardly to a constriction 84, opening into the interior 88, which is slightly smaller than the outer dimension of guide head 28. With needle 20 fixed in a conventional manner in the front of needle rod 16, the needle and body of needle rod 16 together with spring 18 are passed through opening 40. Guide head 28 is then forced through opening 40 past constriction 84 which may be about three to ten thousandths of an inch smaller in diameter than guide head 28. This size differential is selected depending on the materials used, but elastic deformation is the mechanism of choice.

Installation of needle rod 16 in plunger 14 can be done outside the outer body or with the assembled plunger and piston already installed in outer body 12 through opening 46. Plunger 14 is pushed down to about the position of FIG. 2 and a rod introduced through opening 40 to push the needle and front part 24 of the needle rod out the front of outer body 12 where retaining ring 62 can be installed over front part 24 onto and in frictional engagement with back part 22 of the needle rod. The compressed spring 18 tends to pull the retainer ring 62 inside front position 48 of the outer body. A simple cylindrical tool can then be used to seat the back surface 82 of retainer member 62 under and against restriction 72 to hold the needle rod in place. Then the tip member 52 is inserted into the end of outer body 12 and fixed in place, preferably by ultrasonic or spin welding techniques. All that remains is installation of the protective cap and sterilization by low temperature process such as radiation or gas.

It will be noted that all assembly operations are performed axially and without regard to the radial angular orientation of any of the parts. Assembly is all from top and bottom without the need for any lateral movement, an ideal situation for robotic assembly. The needle does not have to be threaded through small openings during assembly so that even if it is slightly bent to one side (needles are seldom straight), it will not hang up during assembly. Only one part is friction fit to another part. No parts have to be spread apart or flexed or hooked together to assemble the device. The only part that is fixed to another part, the tip member, is conveniently exposed at the front of the body.

Figure 6:
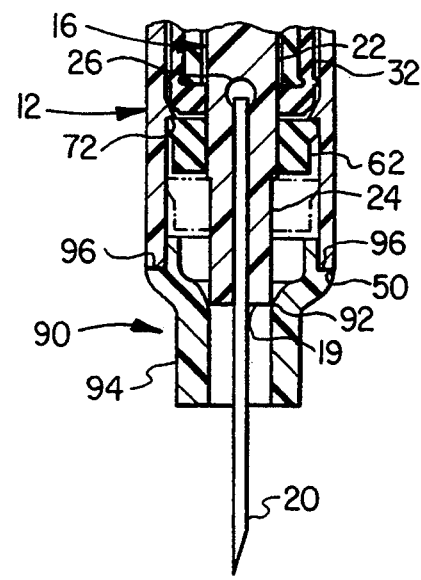
FIG. 6 is a cut-away cross-sectional view of an alternate front of the device wherein a tip member is equipped with shoulders to set it in place.

An alternate tip member 90 is shown in FIG. 6, everything else being like FIGS. 1–5. Tip member 90 has a shoulder 92 in the path of end 19 of needle rod 16 to stop forward movement of needle rod 16. Tip member 90 has a thickened tip extension 94 through which needle 20 is extended in the unretracted position. An annular ledge 96 engages the end 50 of outer body 12 and tip member 90 is fixed thereto. Ledge 96 serves to positively locate tip member 90 during assembly and makes a neater end. The dotted line position of retainer ring 62 illustrates the release position which permits the needle rod to be retracted.

Figure 7:
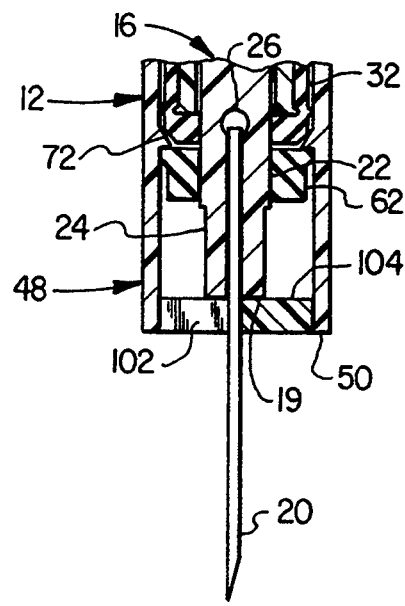
FIG. 7 is a cut-away cross-sectional view of an alternate tip member which serves as a stop in the path of a needle rod.
Figure 8:
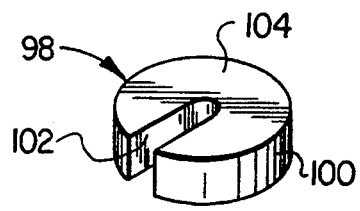
FIG. 8 is a perspective view of the tip member of FIG. 7 with a slot that enables it to be placed over the needle and inserted easily into the tip of the syringe body.

FIGS. 7 and 8 illustrate an alternative tip member 98 which may be used in place of tip member 52. Tip member 98 is a disk having a peripheral outer surface 100 designed to fit within the end of outer body 12. It has upper surface 104. Slot 102 enables disk 98 to be placed over the needle so that the needle doesn't have to be threaded through a small opening. After the retainer 62 is placed on back portion 22 of needle rod 16, and positioned at stops 72, tip member 98 is inserted in the open end of end portion 48 and fixed in place by suitable means. Surface 104 then serves as a stop in the path of the end of the needle rod.

Figure 9:
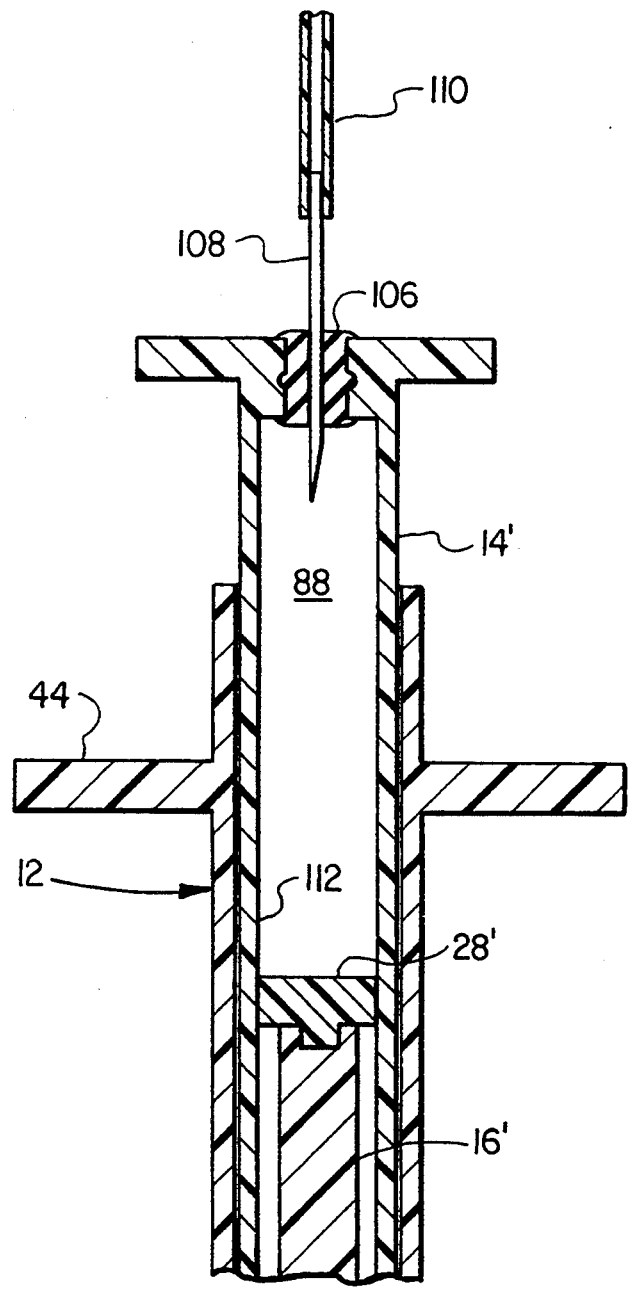
FIG. 9 is an alternative embodiment modified to accept a partial vacuum behind the head of the needle rod to serve as a biasing means.

FIG. 9 represents a modification of the syringe in which modified parts carry a prime with the same reference numeral as the similar part in FIGS. 1 through 8. The front portion of the device is the same as that disclosed in FIGS. 1–8 and the same outer body 12 is used. Plunger $14^1$ is modified in that opening 40 is replaced with an opening having a sealed rubber or elastomeric plug member 106 having the characteristic that it can be punctured by a small, sharp needle 108 which automatically forms a seal when needle 108 is withdrawn. Needle 108 is connected to a vacuum tube 110 which is connected to a source of vacuum and a partial vacuum is drawn in space 88. Needle rod $16^1$ is like needle rod 16 except for a separate elastomeric glide head $28^1$ which is attached to the end thereof. Glide head $28^1$ slidingly seals the inner surface 112 of plunger $14^1$. The vacuum introduced into space 88 serves as a biasing means which operates to provide the retraction force to needle rod $16^1$. Consequently, biasing element spring 18 is not needed and is absent. When retainer member 62 is pushed by the plunger from the back portion 22 to the front portion 24 of needle rod $16^1$, the needle rod is released and the vacuum in chamber 88 causes needle rod $16^1$ and the attached needle to retract into the back end of plunger $14^1$. The vacuum force applied by vacuum chamber 88 substitutes for the retraction force otherwise provided by spring 18.

In the best mode, the syringe components are molded from conventional plastic materials except where otherwise specified. The tip member is preferably force fit into the end of the barrel and fixed in place by sonic welding. It keeps the needle rod from moving forward when the plunger is depressed and keeps the retainer member inside the syringe after retraction. The retainer member is preferably a ring member formed from medical grade rubber or elastomer having a hardness as measured on the Shore D scale of approximately 40 to 50 durometer. Medical grade connotes approval by the applicable regulatory authority and of course all parts of the syringe must be sterilizable. The biasing spring is preferably stainless steel. Because of the seal around the needle rod and the inner walls of the outer barrel provided by the resilient retainer member, the biasing element around the needle rod is separated from the fluid chamber at all positions of the plunger until after retraction occurs. Retraction occurs only after the fluid has been injected and the variable chamber is collapsed by depression of the plunger. Exemplary of the forces involved, for example, the retraction force could be approximately one half pound and the friction ring could require approximately one and one half pounds of force to dislodge it. Forces of this magnitude would not be unusual in retractable syringe technology. The smaller diameter front portion of the needle rod must be long enough so that the retainer member can be moved without interfering with the tip member. The larger diameter back portion of the needle rod behind the front portion is preferably of a constant diameter, although the larger diameter portion only needs to be extant where the retainer ring is installed and could be a different diameter farther back behind the installed retainer member.

I claim:

1. In a single use medical device having a retraction mechanism with a needle for collecting and injecting fluid, an elongate hollow outer body containing a retraction mechanism and a plunger slidable axially in the outer body, the retraction mechanism including a needle holding member having an unretracted extended position wherein the needle is extended from the body while being biased toward a retracted position entirely within the body, a biasing element for applying retraction force to the needle holding member in a retraction direction and a release element capable of holding the needle holding member against the biasing force provided by the biasing element, the release element being triggered to release the needle holding member for retraction of the needle in response to selective movement of the plunger, the improvement comprising:

the needle holding member comprises an elongated needle rod having a needle extending from a front end thereof, said needle rod having a front portion and a back portion wherein said front portion is a smaller than said back portion;

said release element is a separate release element slidingly mounted on the back portion of said needle rod, behind the smaller front portion and held thereon with a friction force that exceeds said retraction force;

said release element cooperates with the outer body to hold the needle rod with the needle extended in the unretracted position while the plunger is movable relative to said outer body to collect or inject fluid;

part of the back portion of said needle rod being positioned within said plunger at all positions of the plunger while moving the plunger during use of the device for collecting and injecting fluid;

retraction is initiated by relative movement of the release element from the back portion to the smaller front portion of the needle rod, caused by force applied by the front of the plunger to the release element at the end of the plunger stroke; and retraction occurs when the release element loses its frictional holding force in excess of said retraction force as a result of the release element being pushed to the smaller front portion of the needle rod whereupon the needle rod is free to retract and moves into said retracted position.

2. The single use medical device of claim 1 wherein a varying chamber for injection fluid is created behind the release element by rearward movement of the plunger away from the release element, said chamber being in fluid communication with an opening in the needle.

3. The single use medical device of claim 2 wherein said biasing element operates inside the plunger to apply said retraction force in the retraction direction to the needle rod.

4. The single use medical device of claim 2 wherein the varying chamber for injection fluid is sealed by the retainer member and by a front head portion of the plunger having a resilient piston which slides with the plunger inside the outer body.

5. The single use medical device of claim 1 wherein during use of the device, with the needle in the extended unretracted position, the back portion of the needle rod passes through the front head portion of the plunger and is sealed thereby.

6. The single use medical device of claim 5 wherein said biasing element is mounted inside the plunger and operates to apply said retraction force in the retraction direction to said needle rod.

7. The single use medical device of claim 6 wherein the interior of the plunger has a support surface for one end of said biasing element and the back end of the needle rod has a sliding guide head and a support surface for the other end of the biasing element, the biasing dement comprising a spring compressible between said support surfaces to provide said retraction force to the needle rod.

8. The single use medical device of claim 7 wherein the plunger has a laterally enlarged back with an axially aligned opening for insertion of the needle rod, the opening having a restricted diameter through which the guide head of the needle rod can be forced in one direction during assembly but prevents the needle rod from exiting thereafter.

9. The single use medical device of claim 1 wherein the outer body has a front end portion from which the needle, in the unretracted position of the needle rod, extends for use;

the front end portion of the outer body being equipped with a tip member having a stop surface located in the path of the needle rod to arrest forward movement of the needle rod.

10. The single use medical device of claim 9 wherein in the unretracted position of the needle, the needle rod has a front end positioned against the stop surface of the tip member to prevent forward movement, and said release element cooperates with a stop surface on the inside of the outer body to prevent reverse movement of the needle rod.

11. The single use medical device of claim 10 wherein the needle member has a portion enclosed within the front of the needle rod, terminating at a fluid opening in the needle rod which is located behind the release element with the needle extended in the unretracted position.

12. The single use medical device of claim 11 wherein the release element is a resilient ring member which simultaneously creates a sliding seal around the needle rod and around the interior of the outer body when said resilient ring member is positioned on the back portion of the needle rod with the needle rod and needle in the unretracted position, thereby establishing the bottom of said variable chamber within the outer body above said resilient ring member.

13. The single use medical device of claim 12 wherein the plunger has a front head portion through which the back portion of the needle rod is sealingly extended into the plunger when the needle is in the extended position for use.

14. The single use medical device of claim 13 wherein a resilient piston on the front head portion of the piston simultaneously slidingly seals the back portion of the needle rod and the inner surface of the outer body, with the needle in the extended position.

15. The single use medical device of claim 13 wherein the resilient piston has a laterally extending face and an opening through which the back portion of the needle rod sealingly passes with the needle rod extended, said face and said resilient ring member coming together to expel substantially all fluid from said variable chamber when the plunger is depressed and thereafter upon further depression, the face of said piston serving to move the ring member from its previous position into a position over said smaller front portion of the needle member, thereby initiating said retraction.

16. A single use syringe having a permanently retractable needle for injecting fluid into a body comprising:

(a) a hollow outer body having a longitudinal axis and being elongated axially between a tip end at the front and a back end and providing a cavity for the fluid;

(b) a movable plunger disposed partially within the hollow outer body, having an internal space and a front portion having a piston mounted thereon in slidable sealed contact with the interior surface of the hollow outer body to form a variable chamber for the fluid below the piston;

(c) a needle rod axially positioned partially within the internal space of the plunger, the needle rod having a front portion extending through the piston, said front portion having an embedded needle and a front end from which said needle protrudes;

(d) a retainer member mounted on the front portion of the needle rod below the piston in contact with the interior surface of the hollow outer body, the retainer member frictionally but slidably engaging the needle rod with a frictional holding force to hold the needle rod in an unretracted position with the needle extended for use;

(e) a biasing means within the plunger applying a retraction force to the needle rod which is less than said frictional holding force;

(f) a stop member in the tip end of said outer body in the path of the front end of the needle rod and a stop above the retainer member to prevent the needle rod from moving axially;

(g) a reduced size portion of the needle rod below said retainer member and above the front end of the needle rod;

(h) whereby, the plunger may be used to draw fluid into a variable chamber above the retainer member and to expel said fluid by depression of the plunger and upon further depression of the plunger after said fluid has been expelled, the retainer member is moved forward to the reduced size portion of the needle rod whereupon the frictional holding force becomes less than the retraction force which automatically causes the needle rod and needle to permanently retract into the syringe.

17. The single use syringe of claim 16 wherein the hollow outer body is a cylindrical barrel and said retainer member has a circular outer surface adapted to slidingly and sealingly contact the interior surface of the cylindrical outer body.

18. The single use syringe of claim 17 wherein said retainer member has a circular outer surface which is smaller in diameter than the interior of the cylindrical body and a circular land which is adapted to slidingly seal the interior surface of said cylindrical outer body.

19. The single use syringe of claim 17 wherein said retainer member is made from a resilient elastomer having a durometer of at least about 40.

20. The single use syringe of claim 16 wherein the front portion of the plunger is in slidingly sealed contact with the needle rod while the needle rod and needle are in the unretracted position with the needle extended for use.

21. The single use syringe of claim 20 wherein the piston on the front portion of the plunger is a resilient piston which simultaneously seals the needle rod and the inner surface of the outer body, with the needle in the extended position.

22. The single use syringe of claim 21 wherein the resilient piston has a laterally extending face and an opening through which the back portion of the needle rod sealingly passes with the needle rod extended, said face and said retainer member coming together to expel substantially all fluid from said variable chamber when the plunger is depressed and thereafter upon further depression, the face of said piston serving to move the retainer member from its previous position to a position over said reduced size portion of the needle rod, thereby initiating retraction.

23. The single use syringe of claim 16 wherein the back end of the needle rod has a glide head which slides loosely in the plunger and provides lateral support for the needle rod in aid of smooth retraction.

24. The single use syringe of claim 17 wherein said retraction force is applied to said guide head by said biasing means.

25. The single use syringe of claim 24 wherein said biasing means comprises an elongated spring surrounding said needle rod.

26. The single use syringe of claim 24 wherein said glide head is a sealing head which slidingly seals the back portion of said plunger, said plunger behind said sealing head being provided with a vacuum chamber which serves to apply said retraction force to said needle rod through said sealing head.

27. A single use syringe having a permanently retractable needle for injecting fluid into a body comprising:
 a syringe body having a back and a front tip portion, the syringe body having an inner surface and an elongated plunger having a piston slidingly mounted for selective movement within the interior of the syringe body;
 an elongated needle rod coaxially mounted within said plunger for positioning in an unretracted position and a retracted position, said needle rod being biased with a retraction force in a retraction direction toward the back of said syringe;
 said needle rod having a front end from which a needle extends;
 a resilient retainer member mounted on the needle rod and spaced behind said front end, said retainer member slidingly and frictionally engaging said elongated needle rod and holding said needle rod with a friction force exceeding said retraction force;
 a variable chamber being defined within said syringe body between said retainer member and said piston and being in fluid communication with said needle;
 stop member in said syringe body to restrain the resilient release member from movement in the retraction direction and establish the needle rod in the unretracted position with the needle extended;
 means for preventing forward movement of the needle rod when the plunger is depressed;
 whereby the needle rod is released for retraction in the retraction direction by depression of the plunger causing forward movement of the retainer member on the needle rod, said forward movement of the retainer member being accompanied by reduction of said frictional holding force and release of the needle rod whereupon the retraction force drives the needle rod and needle to the retracted position in the retraction direction entirely within the syringe.

28. The single use syringe of claim 27 wherein said needle rod includes a glide head comprising a sealing head which slidingly seals the back portion of said plunger, said plunger behind said sealing head being provided with a vacuum chamber which serves to apply said retraction force to said needle rod through said sealing head.

29. A single use syringe having a permanently retractable needle for injecting fluid into a body comprising:
 a hollow syringe body having a tip portion containing means for preventing a needle rod from moving forward;
 a hollow plunger having a front end portion equipped with a piston slidingly sealing the interior of the syringe body and defining the upper boundary of a variable fluid chamber within said syringe body;
 a needle rod having a front end equipped with a needle and being slidingly mounted in the plunger, said needle rod having an unretracted position with the needle extended from the tip portion of the syringe for use and a retracted position wherein said needle rod and needle are withdrawn within the syringe;
 a resilient release element frictionally mounted on the needle rod below the piston and cooperating with a stop in the syringe body to keep the release element from moving backward away from the tip portion of the syringe body, the release element being positioned on the needle rod at an axial location which positions the needle rod against the means for preventing the needle rod from moving forward;
 the resilient release element defining a lower boundary of said variable fluid chamber within said syringe body and being movable to a release position in response to depression of said plunger wherein said resilient release element is released from frictional engagement with said needle rod to initiate retraction of the needle rod and needle to said retracted position;
 a biasing means associated with said plunger to apply a retraction force to said needle rod so that when said resilient release element is released from said needle rod in response to depression of the plunger, said needle rod and said needle are automatically retracted into said syringe.

* * * * *

UNITED STATES PATENT AND TRADEMARK OFFICE
CERTIFICATE OF CORRECTION

PATENT NO. : 5,389,076
DATED : February 14, 1995
INVENTOR(S) : Thomas J. Shaw

It is certified that error appears in the above-indentified patent and that said Letters Patent is hereby corrected as shown below:

Col. 10, line 63, delete "dement" and insert --element--.

Signed and Sealed this

Eighteenth Day of April, 1995

Attest:

BRUCE LEHMAN

*Commissioner of Patents and Trademarks*

*Attesting Officer*